(12) United States Patent
Kamado et al.

(10) Patent No.: US 7,988,762 B2
(45) Date of Patent: Aug. 2, 2011

(54) PROTECTIVE GAS COMPOSITION FOR MAGNESIUM/MAGNESIUM ALLOY PRODUCTION AND COMBUSTION PREVENTING METHOD

(75) Inventors: Shigeharu Kamado, Nagaoka (JP); Hayato Okumura, Nankoku (JP); Daisuke Yamagata, Iwata (JP); Yasuo Hibino, Shiki (JP); Fuyuhiko Sakyu, Iruma-gun (JP)

(73) Assignees: Central Glass Company, Limited, Ube-shi (JP); Nagaoka University of Technology, Nagaoka-shi (JP)

( * ) Notice: Subject to any disclaimer, the term of this patent is extended or adjusted under 35 U.S.C. 154(b) by 370 days.

(21) Appl. No.: 12/095,671

(22) PCT Filed: Nov. 1, 2006

(86) PCT No.: PCT/JP2006/321874
§ 371 (c)(1),
(2), (4) Date: May 30, 2008

(87) PCT Pub. No.: WO2007/063674
PCT Pub. Date: Jun. 7, 2007

(65) Prior Publication Data
US 2010/0257976 A1    Oct. 14, 2010

(30) Foreign Application Priority Data
Dec. 1, 2005    (JP) .................................. 2005-348541

(51) Int. Cl.
*C22B 26/22* (2006.01)
(52) U.S. Cl. ........................................... 75/602; 75/300
(58) Field of Classification Search .................... 75/300, 75/602
See application file for complete search history.

(56) References Cited

U.S. PATENT DOCUMENTS

| | | | |
|---|---|---|---|
| 1,972,317 A | | 9/1934 | Reimers |
| 5,728,902 A * | | 3/1998 | Aoyama et al. ................ 570/136 |
| 5,986,151 A * | | 11/1999 | Van Der Puy ................. 570/175 |
| 6,929,674 B1 | | 8/2005 | Ricketts et al. |
| 2003/0034094 A1 | | 2/2003 | Milbrath et al. |
| 2003/0164068 A1 | | 9/2003 | Milbrath et al. |
| 2005/0241805 A1 | | 11/2005 | Singh et al. |
| 2006/0144190 A1 | | 7/2006 | Sanui et al. |
| 2008/0000647 A1* | | 1/2008 | Luly et al. ........................ 169/46 |
| 2008/0163956 A1* | | 7/2008 | Hibino et al. .................. 148/242 |

FOREIGN PATENT DOCUMENTS

| | | |
|---|---|---|
| CN | 101142043 A | 3/2008 |
| JP | 2002-541999 A | 12/2002 |
| JP | 2004-9110 A | 1/2004 |
| JP | 2004-276116 A | 10/2004 |
| WO | WO 2006/118157 A1 | 11/2006 |

OTHER PUBLICATIONS

J. W. Fruehling, Protective Atmospheres for Melting Magnesium Alloys, AFS Transactions 77, 1969, pp. 159-164.
International Search Report dated Feb. 6, 2007 with English translation (Three (3) pages).
Chinese Office Action dated Nov. 20, 2009, together with English translation (eight (8) pages).
Korean Office Action dated Apr. 28, 2010 (Eight (8) pages).
Co-pending patent U.S. Appl. No. 12/824,637 filed Jun. 28, 2010.

* cited by examiner

*Primary Examiner* — George Wyszomierski
*Assistant Examiner* — Tima M McGuthry-Banks
(74) *Attorney, Agent, or Firm* — Crowell & Moring LLP

(57) ABSTRACT

There is provided a protective gas composition for preventing combustion of a molten magnesium/magnesium alloy, containing a compound selected from the group consisting of 1,1,1,3,3-pentafluoropropane (HFC-245fa), 1,3,3,3-tetrafluoropropene (OHFC-1234ze), methyl 1,1,2,2-tetrafluoroethyl ether (HFE-254pc), which are fluorine-containing organic compounds, and mixtures thereof; and a carrier gas.

4 Claims, No Drawings

PROTECTIVE GAS COMPOSITION FOR MAGNESIUM/MAGNESIUM ALLOY PRODUCTION AND COMBUSTION PREVENTING METHOD

TECHNICAL FIELD

The present invention relates to a protective gas composition for preventing combustion in the production of a magnesium/magnesium alloy molten at high temperature, and a method for preventing combustion of a molten magnesium/magnesium alloy.

BACKGROUND OF THE INVENTION

Magnesium and magnesium alloy have superior characteristics as a light-weight structural member, since they are light in weight (specific gravity: 1.7) and large in specific strength. However, they have not been used widely so far, since the cost related to the production (or the energy necessary for the production) and the like are relatively high. Upon producing magnesium and magnesium alloy, since magnesium and magnesium alloy molten at high temperature react vigorously with oxygen in the air and combust, it is necessary to have special facilities and techniques for their melting and casting. As one of ignition proof effect provisions for magnesium alloy, it has been tried to provide metal itself with ignition proof effect by adding calcium (Ca), beryllium (Be) or the like, but it is not necessarily sufficient. Besides, a method of pouring a protective flux onto a molten metal, a method of covering a metal surface with an inert gas such as helium, argon or nitrogen gas, or a method of covering it with a protective gas that forms a protective film on the metal surface has been tried, in order to prevent an abrupt oxidation (combustion) of molten magnesium and magnesium alloy.

As a protective gas in the magnesium and magnesium alloy production steps, sulfur dioxide ($SO_2$) has been historically used many times, since it has a low price and is easily available. However, it is limited in use environment and equipment, since it is high in bad odor, metal corrosiveness and toxicity. In place of this, sulfur hexafluoride ($SF_6$), which is low in toxicity and odorless, has been widely used, since it has no flammability and an advantageous effect at a relatively low concentration [Non-patent Publication 1]. $SF_6$, however, has a global warming potential (GWP) that is about 24,000 times that of carbon dioxide ($CO_2$) and furthermore has a very long atmospheric lifetime of 3,200 years. Therefore, it is an object of limitation as a warming substance in Kyoto Protocol. Magnesium and magnesium alloy become energy-saving materials, since they contribute to weight reduction when used as structural members of automobiles and the like. However, $SF_6$ ejected during the production is a substance that has a great impact on global warming, thereby canceling out the energy-saving part. Thus, there is a strong demand for the development of a protective gas alternative to $SF_6$.

Various fluorine-series compounds have been proposed as protective gases alternative to $SF_6$. For example, in Patent Publication 1, Japanese Patent Application Publication 2002-541999, difluoromethane (HFC-32), pentafluoroethane (HFC-125), 1,1,1,2-tetrafluoroethane (HFC-134a), difluoroethane (HFC-152a), heptafluoropropane (HFC-227ea), methoxy-nonafluoroethane (HFE-7100), ethoxy-nonafluoroethane (HFE-7200), and dihydrodecafluoropropane (HFC-43-10me) are cited. Of these, a combination of HFC-134a and dry air is recommended as a preferable composition. Furthermore, in Patent Publication 2, US Patent Application Publication 2003/0034094; Patent Publication 3, US Patent Application Publication 2003/0164068; and Patent Publication 4, Japanese Patent Application Publication 2004-276116, perfluoroketones, ketone hydrides and their mixtures are cited as protective gases. Specifically, pentafluoroethyl-heptafluoropropylketone ($C_2F_5(CO)C_3F_7$) is shown as an example. Furthermore, boron trifluoride ($BF_3$), silicon tetrafluoride ($SiF_4$), nitrogen trifluoride ($NF_3$), and sulfuryl fluoride ($SO_2F_2$) are cited in Patent Publication 5, U.S. Pat. No. 1,972,317.

Non-patent Publication): J. W. Fruehling, J. D. Hanawalt, Trans. AFS 77, 159 (1969)

Patent Publication 1: Japanese Patent Application Publication 2002-541999

Patent Publication 2: US Patent Application Publication 2003/0034094

Patent Publication 3: US Patent Application Publication 2003/0164068

Patent Publication 4: Japanese Patent Application Publication 2004-276116

Patent Publication 5: U.S. Pat. No. 1,972,317

SUMMARY OF THE INVENTION

Substances proposed hitherto as protective gases alternative to $SF_6$ had problems that they need special facilities and equipment and care for handling upon their use in magnesium and magnesium alloy production site, due to that they themselves have high toxicity, that they produce toxic gases such as perfluoroisobutene by contact with molten magnesium or magnesium alloy, that they have high prices, or that they have high boiling points, etc. To solve these problems, there are a demand for a novel protective gas composition and a demand for adjustment of the method for use.

It is an object of the present invention to provide a novel protective gas composition that has a low toxicity, a relatively low global warming potential (GWP), that is, a low impact on the environment, and a low boiling point, as a protective gas that is effective for preventing combustion in magnesium or magnesium alloy production, and to provide a method using it under proper conditions, such as concentration and flow rate, in a molten metal temperature region from low temperature region to high temperature region.

The present inventors have eagerly examined various fluorine-containing organic compounds to solve the above task and have reached the present invention by using a protective gas composition that has a relatively low GWP, a low toxicity and a low boiling point and by finding proper conditions, such as concentration and flow rate, in a molten metal temperature region of wide-scale magnesium and magnesium alloys from low temperature region to high temperature region (typically 600-850° C.).

According to the present invention, there is provided a protective gas composition for preventing combustion of a molten magnesium/magnesium alloy, comprising a compound selected from the group consisting of 1,1,1,3,3-pentafluoropropane (HFC-245fa), 1,3,3,3-tetrafluoropropene (OHFC-1234ze), methyl 1,1,2,2-tetrafluoroethyl ether (HFE-254pc), and mixtures thereof; and a carrier gas.

Furthermore, according to the present invention, there is provided a method for preventing combustion of a molten magnesium/magnesium alloy, which is characterized in that, in a magnesium or magnesium alloy production, the above gas composition is allowed to flow onto a surface of a molten metal molten at 600-850° C.

DETAILED DESCRIPTION

A protective gas composition of the present invention, which contains a fluorine-containing organic compound and a carrier gas, is a gas composition for protecting a molten magnesium/magnesium alloy, the composition having a relatively low GWP as compared with conventional protective gases, low toxicity, and little production of decomposable toxic gases. It can be used in a wide-scale molten metal temperature region of low temperature region to high temperature region of 600-850° C. Furthermore, it is possible to reduce the environmental load and to increase safety upon operation.

Fluorine-containing organic compounds used in the present invention are desirably remarkably smaller, preferably 1,000 or less, in GWP relative to $SF_6$ used hitherto, from the viewpoint of global environmental protection. From such viewpoint, HFC-125, HFC-134a, HFC-227ea, etc. are relatively large in GWP. Therefore, it is difficult to say that they are preferable. Although HFC-152a and HFC-32 have low GWP's, these compounds are small in effective F content in the molecule and high in combustibility. Therefore, there are difficulties in terms of the effect of preventing combustion of molten magnesium or magnesium alloy and in terms of handling. Thus, it is difficult to say that they are preferable. Although they are expected to have high protective effects, high toxicity compounds, such as $BF_3$, $SiF_4$, $NF_3$ and $SO_2F_2$, are not necessarily preferable from the viewpoints of operator health side and safety upon use.

Although the protecting mechanism (ignition proof effect) of molten magnesium/magnesium alloy by $SF_6$ is not clear, there is a report (S. P. Cashion et. al., J. Light Metals, 2, 43 (2002); G. Pettersen, et. al., Materials Science and Engineering, A332, 285 (2002)) that, as shown in the following reaction, it is achieved by forming a firm, dense film made of a mixture of crystalline MgO and amorphous $MgF_2$, on the surface of the molten metal. In this case, it is shown that the protective film is firstly magnesium oxide (MgO), and it reacts further with $SF_6$ to become magnesium fluoride ($MgF_2$). That is, it is considered that F carries out an important function in protecting molten magnesium/magnesium alloy. Therefore, one having a greater F content in the protective gas molecule is considered to be advantageous to form the protective film.

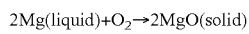

2Mg(liquid)+$O_2$→2MgO(solid)

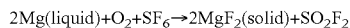

2Mg(liquid)+$O_2$+$SF_6$→2$MgF_2$(solid)+$SO_2F_2$

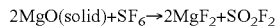

2MgO(solid)+$SF_6$→2$MgF_2$+$SO_2F_2$

In the present invention, HFC-245fa, OHFC-1234ze and HFE-254pc were selected as the protective gases, since they have relatively low GWP's and relatively large F contents in the molecules. Regarding GWP 100 year value, it is assumed that HFC-245fa is 950, HFE-254pc is 30, and OHFC-1234ze is about 10, and each of which is sufficiently smaller as compared with $SF_6$. Here, OHFC is an abbreviation of Olefine HydroFluoroCarbon and represents an unsaturated HFC having a double bond in the molecule. These unsaturated compounds are generally high in reactivity with OH radicals in the atmosphere, and thereby their GWP's become extremely low. Therefore, they have been represented by OHFC to have a distinction from HFC.

HFC-245fa is obtained, for example, by subjecting 1,1,1,3,3-pentachloropropane to a two-step fluorination by anhydrous hydrofluoric acid.

OHFC-1234ze can be obtained by treating 1,1,1,3,3-pentafluoropropane with potassium hydroxide or the like, or by pyrolyzing it in gas phase in the presence or absence of catalyst, or by fluorinating 1-chloro-3,3,3-trifluoropropene in gas phase in the presence of catalyst. The obtained OHFC-1234ze is a mixture of structural isomers of trans configuration (E) and cis configuration (Z), but it is possible to use either E configuration or Z configuration or a mixture of both as the target protective gas. In the present invention, the E configuration, which is easy in handling and has a low boiling point, was used, since it can be used as gas at ordinary temperature and ordinary pressure. HFE-254pc can be obtained by adding methanol to tetrafluoroethylene in the presence of a base catalyst.

It is preferable that the protective gas is in gas or easily vaporized at ordinary temperature and ordinary pressure. The boiling points of respective compounds of the present invention are HFC-245fa (15° C.), OHFC-1234ze(E) (−16° C.), OHFC-1234ze(Z) (10° C.), and HFE-254pc (37° C.). These fluorine-containing organic compounds can be used singly or in mixture.

As the carrier gas, an inert gas is selected. Dry air, carbon dioxide, argon, helium, neon, krypton, xenon, nitrogen, and mixtures thereof are preferable. Of these gases, particularly carbon dioxide, dry air, or a mixed gas of carbon dioxide and dry air is preferable. In terms of the global warming prevention effect, air, argon, helium and nitrogen are preferable to carbon dioxide having GWP, and nitrogen, which is nonflammable and low-priced, is particularly practically preferable.

The concentration of the protective gas in the carrier gas can take 0.005-5 volume %, preferably 0.01-1 volume %. If the protective gas concentration is too low, the formation of $MgF_2$ by the reaction with molten magnesium becomes small. With this, it is difficult to obtain the protective effect. If it is excessive, not only the effect does not appear in proportion to the concentration, but also, on the contrary, decomposition products derived from the protective gas increase, thereby giving adverse effects on external appearance, property and the like of the magnesium or magnesium alloy, and adverse influences appear in working environment. However, in the case of using dry air as the carrier gas, for example, a concentration outside of the combustion range should be used in HFE-254pc, which is a flammable compound. Here, the combustion range of HFE-254pc is 5.4-24.4 volume %, and a protective gas composition used in general is not particularly problematic.

The method of preventing combustion of molten magnesium/magnesium alloy is conducted by allowing the above protective gas composition to flow onto the surface of the molten metal molten at around 600-850° C. in the magnesium and magnesium alloy productions.

The lower limit of the used temperature of the protective gas composition of the present invention is not particularly limited. For example, it is also possible to allow the protective gas composition to flow at around 400° C. However, it shows its performance preferably at 600-850° C., which is casting temperature of Mg or Mg alloy in general. In particular, the use in a temperature region of roughly 620-800° C. is preferable. In particular, a temperature region of 630-760° C. is particularly preferable in respect of that a superior ignition proof effect performance is remarkable as compared with the existing $SF_6$ and the like.

It is possible to use the protective gas composition of the present invention itself by making it continuously flow onto the upper part of the molten magnesium or magnesium alloy through previously adjusting the concentration or through separately adjusting each gas flow rate and mixing them to have the target concentration. It is preferable to provide a plurality of gas outlets such that the protective gas composition is uniformly brought into contact with the molten metal surface and to set size, direction, position and the like of the opening to have flows with evenness of each flow rate.

As one of embodiments is shown as an example, it can be conducted by putting magnesium/magnesium alloy into an apparatus having a crucible equipped at its upper part with a protective gas composition introducing pipe and then by making the protective gas composition, which has been introduced from the above protective gas composition introducing pipe, flow. A furnace lid is provided above the molten metal, and the uses with the furnace lid closed and open are possible. Upon this, there occur differences in ignition proof effect by protective gas concentration, flow rate of protective gas composition, molten metal temperature, and the like. In one that is insufficient in ignition proof effect, an ignition source is generated on the molten metal surface, and it grows and continues to combust. If ignition proof effect is improved, an ignition generated on the molten metal surface turns into a condition where it does not grow. One with a sufficient ignition proof effect does not combust at all. That is, it can be said that those except a case where it continues to combust have substantial ignition proof effects. As a standard in terms of time, one having an ignition proof effect of 180 seconds or longer is particularly preferable.

Regarding flow rate and flow velocity of the protecting gas composition, the optimum values are determined in relation to the protective gas concentration and composition of magnesium alloy; molten metal temperature; the area of molten metal surface; the number, shape, size and distribution of the gas introducing opening; and the like. Therefore, it is necessary to conduct an optimization in each apparatus.

Regarding the protective gas flow rate, which becomes an effective factor of ignition proof effect, it apparently depends on the molten metal area. Therefore, "the protective gas flow rate per molten metal unit area (herein after referred to as SGF, too)" can take 5-5000 mL/min/m$^2$, preferably 30-3000 mL/min/m$^2$. If flow rate of the protective gas is too low, the formation of MgF$_2$ by the reaction with molten magnesium becomes small. With this, it is difficult to obtain the protective effect. If it is excessive, decomposition products derived from the protective gas increase to damage external appearance, property, and the like and to increase global warming effect, although it is relatively small. Thus, it is not preferable. Flow rate of the protective gas composition and protective gas flow rate per molten metal unit area are effective with smaller amounts in case that the furnace lid above molten metal is closed, than it is open.

In the combustion preventing method of the present invention, the management of flow velocity of the protective gas composition is also important. An increase of the protective gas concentration or the protective gas flow rate per molten metal unit area is also a method for improving ignition proof effect. Furthermore, it is possible to obtain a large ignition proof effect by increasing flow velocity of the protective gas composition. In particular, in case that a fresh magnesium surface increases after dross removal or the like, it is preferable to increase flow velocity. Each protective gas of the present invention is higher than SF$_6$ in reactivity and reacts locally and is consumed. Therefore, it is considered that it spreads over the molten metal entirety to increase ignition proof effect by increasing flow velocity of low concentration gas than increasing concentration.

This trend is conspicuous, as molten metal temperature becomes high. For example, in the case of using a protective gas composition of the same concentration using the same protective gas, it can be improved by increasing flow velocity, even if at a flow velocity ignition proof effect is found at 650° C., but not found at 750° C.

That is, in the combustion preventing method of the present invention, it is possible to effectively prevent combustion by allowing the protective gas composition to flow at a flow velocity that is sufficient for producing ignition proof effect, while managing the protective gas concentration and/or the protective gas flow rate per molten metal unit area. It can be achieved by regulating flow rate to have an ignition proof effect for, for example, 180 seconds or longer.

As shown in the after-mentioned examples, a particularly important scale as "flow rate" here is "protective gas flow rate in molten metal unit area (mL/min/m$^2$) (SGF)". This SGF is a value obtained by dividing the protective gas flow rate (mL/min) by molten metal surface area A (m$^2$).

SGF of the protective gas to be used depends also on the type of carrier gas, sealing property of melting furnace, and operation conditions. For example, in the case of using CO$_2$ and N$_2$ as carrier gases, they are as follows. In these cases, it is preferable to make flow rate of the carrier gas roughly 1000 or more times that of the protective gas to secure a sufficient flow velocity.

When OHFC-1234ze is used as the protective gas, it is preferable that SGF has the following values as a general rule.
A temperature region that is lower than 680° C. (e.g., not lower than 400° C. and lower than 680° C.): 10-1000 (mL/min/m$^2$). 20-500 (mL/min/m$^2$) is more preferable.
A temperature region that is not lower than 680° C. and lower than 720° C.: 20-1500 (mL/min/m$^2$). In particular, 30-600 (mL/min/m$^2$) is more preferable.
A temperature region that is not lower than 720° C. and lower than 760° C.: 30-5000 (mL/min/m$^2$). In particular, 50-2500 (mL/min/m$^2$) is more preferable.
A temperature region not lower than 760° C.: 100 (mL/min/m$^2$) or greater.

With these SGF values, ignition proof effect tends to stably be maintained for a long time (e.g., 180 seconds) (see the after-mentioned examples). However, even if SGF is lower than the above lower limit, ignition proof effect itself is shown. Therefore, it is possible to set SGF value in accordance with the level of the required ignition proof effect. Even if SGF is higher than the above upper limit, ignition proof effect performance itself does not have problems, but it is not preferable economically and from environmental aspect.

When HFC-245fa is used as the protective gas, it is preferable that SGF has the following values as a general rule.
A temperature region that is lower than 680° C. (e.g., not lower than 400° C. and lower than 680° C.): 10-800 (mL/min/m$^2$). 10-400 (mL/min/m$^2$) is more preferable.
A temperature region that is not lower than 680° C. and lower than 720° C.: 20-1000 (mL/min/m$^2$). In particular, 30-500 (mL/min/m$^2$) is more preferable.
A temperature region that is not lower than 720° C. and lower than 760° C.: 30-2000 (mL/min/m$^2$). In particular, 40-1000 (mL/min/m$^2$) is more preferable.
A temperature region not lower than 760° C.: 100 (mL/min/m$^2$) or greater.

With these SGF values, ignition proof effect tends to stably be maintained for a long time (e.g., 180 seconds) (see the after-mentioned examples). However, even if SGF is lower than the above lower limit, ignition proof effect itself is shown. Therefore, it is possible to set SGF value in accordance with the level of the required ignition proof effect. Even if SGF is higher than the above upper limit, ignition proof effect performance itself does not have problems, but it is not preferable economically and from environmental aspect.

When HFC-254 pc is used as the protective gas, it is preferable that SGF has the following values as a general rule.
A temperature region that is lower than 680° C. (e.g., not lower than 400° C. and lower than 680° C.): 10-1000 (mL/min/m$^2$). 20-500 (mL/min/m$^2$) is more preferable.

A temperature region that is not lower than 680° C. and lower than 720° C.: 20-1500 (mL/min/m$^2$). In particular, 30-600 (mL/min/m$^2$) is more preferable.

A temperature region that is not lower than 720° C. and lower than 760° C.: 30-1500 (mL/min/m$^2$). In particular, 50-1000 (mL/rain/m$^2$) is more preferable.

A temperature region not lower than 760° C.: 100 (mL/min/m$^2$) or greater.

With these SGF values, ignition proof effect tends to stably be maintained for a long time (e.g., 180 seconds) (see the after-mentioned examples). However, even if SGF is lower than the above lower limit, ignition proof effect itself is shown. Therefore, it is possible to set SGF value in accordance with the level of the required ignition proof effect. Even if SGF is higher than the above upper limit, ignition proof effect performance itself does not have problems. However, economical load increases, and it is not preferable from environmental aspect, since the unreacted gas and decomposed gases increase.

Even if firing occurs locally by using the above SGF, it is possible to achieve ignition proof effect by suitably increasing the carrier gas (by increasing flow velocity).

As mentioned above, the GWP value of the protective gas of the present invention is sufficiently smaller than that of $SF_6$. Therefore, in the case of using the ignition proof effect provision method of the present invention, a drastic reduction of the GWP value can be expected. As compared with the case of using conventional $SF_6$ gas (provided that $SF_6$ of 0.2 volume % is used relative to the carrier gas 2 L/min), the warming effect reduction rate can be calculated at about 90% or greater, and thereby it is possible to drastically reduce global warming effect.

It is possible to use the protective gas composition of the present invention itself by allowing it to flow onto the upper part of the molten magnesium or magnesium alloy through previously adjusting the concentration or through separately adjusting each gas flow rate and mixing them to have the target concentration. It is preferable to provide a plurality of gas outlets such that the protective gas composition is uniformly brought into contact with the molten metal surface and to set size, direction, position and the like of the opening to have flows with evenness of each flow rate.

In molten metal temperature of magnesium or magnesium alloy, for example, a relatively low temperature range of 650° C. corresponds to hot chamber die casting, a middle temperature range of 700° C. corresponds to cold chamber die casting and sand mold and metallic mold castings of general magnesium alloys (Mg—Al—Zn alloy and the like), and a high temperature range of 800° C. corresponds to sand mold and metallic mold castings of zirconium-containing, special magnesium alloys (Mg—Zn—Zr, Mg-rare-earth element-Zr series alloy, and the like). Therefore, a protective gas composition having ignition proof effect in all of these temperature ranges is useful in industry. The protective gas composition of the present invention may be applied to various uses, since it has ignition proof effect in a magnesium or magnesium alloy molten metal temperature range of 600-850° C. by adjusting the protective gas concentration and the protective gas flow rate and flow rate of the protective gas composition per molten metal unit area.

Moisture in the atmosphere around the melting furnace and in the carrier gas should be avoided to the utmost, since it produces HF by a reaction with a fluorine moiety in the carrier gas. It is possible to monitor moisture in the carrier gas by managing dew point of the gas.

EXAMPLES

In the following, it is specifically explained by citing examples of the present invention, but the present invention is not limited by these examples.

Example 1

An iron (SS) crucible (diameter: 150 mm, height: 250 mm) equipped at its upper part with protective gas introducing pipes (two stainless steel (SUS304) pipes having a diameter of 6 mm) was charged with 3.5 kg of a magnesium alloy (AZ91D). While the furnace lid was closed, $CO_2$ at 2 L/min and $SF_6$ at 25 mL/min were allowed to flow, and AZ91D was melted, followed by stirring to have a molten metal temperature of 650° C. Protective gas introducing pipe outlets were installed at a position having a height of 30 mm from the molten metal surface.

The gas was changed from $SF_6$ to OHFC-1234ze(E), and flow rates of $CO_2$ and OHFC-1234ze(E) were respectively set at 2 L/min and 10 mL/min. This was maintained for 10 min. Then, $CO_2$ and OHFC-1234ze(E) flow rates were set at predetermined amounts, and the furnace lid was opened. A film produced on the molten metal surface was removed, and the molten metal surface was observed for 0-180 seconds (the approximate time necessary for taking the molten metal out) and recorded.

In case that the molten metal surface was not combusted, $CO_2$ and OHFC-1234ze(E) flow rates were respectively decreased in stages, and observations were conducted at predetermined amounts.

Then, the molten metal temperature was changed to 700° C., 750° C. and 800° C., and $CO_2$ and the intended gas flow rates were respectively changed in stages. Observations were conducted at predetermined amounts. Flow rate of OHFC-1234ze was regulated by a mass flow meter, and the other gases were respectively conducted by using a flow meter. The protective gas composition was used by mixing both gases in a glass mixer. The results are shown in Table 1.

TABLE 1

Ignition Proof Effect of OHFC-1234ze(E)
OHFC-1234ze(E) (GWP100 = 10)

| | | Flow Rate | | | | | | | | |
|---|---|---|---|---|---|---|---|---|---|---|
| Molten Metal | $CO_2$ | Protective Gas | Protective Gas Conc. | Time [s] | | | | | | |
| Temp. (° C.) | (L/min) | (mL/min) | (%) | 0 | 30 | 60 | 90 | 120 | 150 | 180 |
| 650 | 6 | 6.05 | 0.10 | ○ | Δ | Δ | Δ | Δ | Δ | Δ |
| | 4 | 3.95 | 0.09 | ○ | ○ | ○ | ○ | ○ | ○ | ○ |

TABLE 1-continued

Ignition Proof Effect of OHFC-1234ze(E)
OHFC-1234ze(E) (GWP100 = 10)

| Molten Metal | Flow Rate | | Protective Gas Conc. | Time [s] | | | | | | |
|---|---|---|---|---|---|---|---|---|---|---|
| | $CO_2$ | Protective Gas | | | | | | | | |
| Temp. (° C.) | (L/min) | (mL/min) | (%) | 0 | 30 | 60 | 90 | 120 | 150 | 180 |
| 700 | 8 | 7.89 | 0.10 | ○ | ○ | ○ | ○ | ○ | ○ | ○ |
| | 6 | 18.15 | 0.30 | ○ | ○ | ○ | ○ | ○ | ○ | ○ |
| | 6 | 6.05 | 0.10 | ○ | ○ | ○ | Δ | Δ | Δ | Δ |
| | 4 | 19.99 | 0.51 | ○ | ○ | X | X | X | X | X |
| 750 | 8 | 40.24 | 0.51 | ○ | ○ | ○ | ○ | ○ | ○ | ○ |
| | 8 | 24.20 | 0.30 | ○ | ○ | ○ | ○ | ○ | ○ | ○ |
| | 8 | 7.89 | 0.10 | ○ | ○ | ○ | ○ | X | X | X |
| | 6 | 30.25 | 0.50 | ○ | ○ | ○ | ○ | ○ | X | X |
| 800 | 8 | 40.24 | 0.51 | ○ | ○ | ○ | ○ | ○ | ○ | ○ |
| | 8 | 24.20 | 0.30 | ○ | ○ | X | X | X | X | X |
| | 8 | 7.89 | 0.10 | ○ | ○ | X | X | X | X | X |
| | 6 | 30.25 | 0.50 | ○ | ○ | ○ | X | X | X | X |

Notations of Table 1 were according to the following standards.
○: one that does not combust (pass).
Δ: one in which an ignition source is generated, but burns out immediately or does not grow (pass).
X: one in which an ignition source grows and continues to burn.
One was judged as pass, in which no combustion occurs for 180 seconds, or, even if an ignition source is generated, it does not spread.

In Table 1, that flow rate of the protective gas composition of the carrier gas ($CO_2$)+the protective gas (protective gas composition flow rate per molten metal unit area) is important is understood from that, in the experiment of 700° C., $CO_2$ 6 L/min+the protective gas 0.10% is higher than $CO_2$ 4 L/min+ the protective gas 0.51% in ignition proof effect. That is, even if the protective gas concentration is low, a high ignition proof effect is obtained in case that flow rate of the protective gas composition is large. This trend is also found in the experiment of 750° C. Thus, in the present invention, from the viewpoint of ignition proof effect of the protective gas, flow rate of the protective gas composition (or flow velocity, if the introducing pipe diameter is the same) is more important than the protective gas concentration.

Example 2

The protective gas composition was changed to $CO_2$ and HFC-245fa, and the experiments were conducted as in Example 1. To stabilize vaporization of HFC-245fa, the storage cylinder and the line were heated to about 40° C. The results are shown in Table 2.

TABLE 2

Ignition proof Effect of HFC-245fa
HFC-245fa (GWP100 = 950)

| Molten Metal | Flow Rate | | Protective Gas Conc. | Time [s] | | | | | | |
|---|---|---|---|---|---|---|---|---|---|---|
| | $CO_2$ | Protective Gas | | | | | | | | |
| Temp. (° C.) | (L/min) | (mL/min) | (%) | 0 | 30 | 60 | 90 | 120 | 150 | 180 |
| 650 | 4 | 4.05 | 0.09 | ○ | ○ | ○ | ○ | ○ | ○ | ○ |
| | 2 | 4.05 | 0.18 | ○ | ○ | ○ | ○ | ○ | ○ | ○ |
| | 2 | 1.92 | 0.12 | ○ | ○ | ○ | ○ | ○ | ○ | ○ |
| | 2 | 1.07 | 0.06 | ○ | ○ | ○ | X | X | X | X |
| 700 | 4 | 20.02 | 0.51 | ○ | ○ | ○ | ○ | ○ | ○ | ○ |
| | 4 | 4.05 | 0.09 | ○ | ○ | ○ | ○ | ○ | ○ | ○ |
| | 4 | 1.92 | 0.06 | ○ | ○ | ○ | X | X | X | X |
| 750 | 4 | 20.02 | 0.51 | ○ | ○ | ○ | ○ | ○ | ○ | ○ |
| | 4 | 4.05 | 0.09 | ○ | ○ | X | X | X | X | X |
| | 6 | 5.96 | 0.01 | ○ | X | X | X | X | X | X |
| | 6 | 18.11 | 0.30 | ○ | ○ | ○ | ○ | ○ | X | X |
| | 8 | 8.09 | 0.10 | ○ | ○ | ○ | ○ | ○ | ○ | ○ |
| 800 | 8 | 24.07 | 0.30 | ○ | ○ | ○ | ○ | ○ | ○ | ○ |
| | 8 | 15.98 | 0.19 | ○ | ○ | ○ | ○ | ○ | ○ | ○ |
| | 8 | 8.09 | 0.10 | ○ | ○ | ○ | ○ | ○ | ○ | ○ |

Notations of Table 2 were according to the following standards.
○: one that does not combust (pass).
Δ: one in which an ignition source is generated, but burns out immediately or does not grow (pass).
X: one in which an ignition source grows and continues to burn.
One was judged as pass, in which no combustion occurs for 180 seconds, or, even if a fire source is generated, it does not spread.

In Table 2, a trend similar to that of Table 1 is found from the results of 750° C., $CO_2$ 6 L/min+the protective gas 0.30% and $CO_2$ 8 L/min+the protective gas 0.10%.

Example 3

The protective gas composition was changed to $CO_2$ and HFE-254pc, and the experiments were conducted as in Example 1. The results are shown in Table 3.

TABLE 3

Ignition Proof Effect of HFE-254pc
HFE-254pc (GWP100 = 30)

| Molten Metal Temp. (°C.) | $CO_2$ (L/min) | Flow Rate Protective Gas (mL/min) | Protective Gas Conc. (%) | 0 | 30 | 60 | Time [s] 90 | 120 | 150 | 180 |
|---|---|---|---|---|---|---|---|---|---|---|
| 650 | 4 | 20.10 | 0.51 | ○ | ○ | ○ | ○ | ○ | ○ | ○ |
|  | 4 | 12.04 | 0.30 | ○ | ○ | ○ | ○ | ○ | ○ | ○ |
|  | 4 | 4.00 | 0.09 | ○ | ○ | ○ | ○ | ○ | ○ | ○ |
| 700 | 6 | 6.01 | 0.10 | Δ | Δ | Δ | Δ | Δ | Δ | Δ |
|  | 4 | 20.10 | 0.49 | Δ | Δ | Δ | Δ | Δ | Δ | Δ |
|  | 4 | 12.04 | 0.30 | Δ | Δ | Δ | Δ | Δ | Δ | Δ |
| 750 | 6 | 18.05 | 0.30 | Δ | Δ | Δ | Δ | Δ | Δ | Δ |
|  | 6 | 6.01 | 0.10 | Δ | Δ | Δ | Δ | Δ | Δ | Δ |
|  | 4 | 20.10 | 0.51 | Δ | Δ | Δ | Δ | Δ | Δ | Δ |
|  | 4 | 12.04 | 0.30 | Δ | X | X | X | X | X | X |
| 800 | 6 | 30.15 | 0.50 | Δ | Δ | Δ | Δ | Δ | Δ | Δ |
|  | 6 | 18.05 | 0.30 | Δ | Δ | Δ | Δ | Δ | Δ | Δ |
|  | 6 | 6.01 | 0.10 | Δ | X | X | X | X | X | X |
|  | 4 | 20.10 | 0.51 | Δ | X | X | X | X | X | X |

Notations of Table 3 were according to the following standards.
○: one that does not combust (pass).
Δ: one in which an ignition source is generated, but burns out immediately or does not grow (pass).
X: one in which an ignition source grows and continues to burn.
One was judged as pass, in which no combustion occurs for 180 seconds, or, even if an ignition source is generated, it does not spread.

In Table 3, a trend similar to those of Tables 1 and 2 is found from the results of 750° C., $CO_2$ 6 L/min+the protective gas 0.10% and $CO_2$ 4 L/min+the protective gas 0.30%. That is, each of the protective gases of the present invention is higher than $SF_6$ in reactivity and is consumed by a local reaction. Therefore, the protective gas spreads over the molten metal surface entirety by increasing the gas flow velocity rather than increasing concentration, thereby increasing ignition proof effect.

The relationship between the protective gas minimum flow rate (shown as examples) for producing ignition proof effect and the warming effect reduction rate, based on Examples 1-3, is shown in Table 4.

The protective gas minimum flow rate represents the protective gas flow rate in the experiments in which a judgement of ○ (one that does not combust) or Δ (one in which an ignition source is generated, but burns out immediately or does not grow) was made for 180 seconds. That is, it indicates that a particularly high ignition proof effect can be maintained by maintaining flow rate of the protective gas to be not lower than these values. (However, it is not limited by these values.)

Regarding warming effect reduction rate, reduction rate was calculated relative to the use of $CO_2$ gas 2 L/min+0.2% $SF_6$. GWP of OHFC-1234ze(E) was assumed to be 10, about 1/100 of GWP of HFC-245fa.

TABLE 4

Protective Gas Minimum Flow Rate for Producing Ignition proof Effect and Warming Effect Reduction Rate
A = 0.01767 m²

| Protective Gas | Molten Metal Temp. (°C.) | $CO_2$ Flow Rate (L/min) | Protective Gas Conc. (%) | Protective Gas Flow Rate (mL/min) | Protective Gas Flow Rate per Molten Metal Unit Area (mL/min/m²) | Warming Effect Reduction Rate (%) |
|---|---|---|---|---|---|---|
| OHFC-1234ze | 650 | 4 | 0.1 | 3.95 | 223.5 | 98.6 |
|  | 700 | 6 | 0.1 | 6.05 | 342.4 | 97.9 |
|  | 750 | 8 | 0.3 | 24.20 | 1369.6 | 97.1 |
|  | 800 | 8 | 0.5 | 40.24 | 2277.3 | 97.0 |
| HFC-245fa | 650 | 2 | 0.1 | 1.92 | 108.7 | 97.4 |
|  | 700 | 4 | 0.1 | 4.05 | 229.2 | 94.8 |

TABLE 4-continued

Protective Gas Minimum Flow Rate for Producing Ignition proof Effect and
Warming Effect Reduction Rate
$A = 0.01767 \text{ m}^2$

| Protective Gas | Molten Metal Temp. (° C.) | $CO_2$ Flow Rate (L/min) | Protective Gas Conc. (%) | Protective Gas Flow Rate (mL/min) | Protective Gas Flow Rate per Molten Metal Unit Area (mL/min/m²) | Warming Effect Reduction Rate (%) |
|---|---|---|---|---|---|---|
| HFE-254pc | 750 | 8 | 0.1 | 8.09 | 457.8 | 89.5 |
| | 800 | 8 | 0.1 | 8.09 | 457.8 | 89.5 |
| | 650 | 4 | 0.1 | 4.00 | 226.4 | 98.5 |
| | 700 | 6 | 0.1 | 6.01 | 340.1 | 97.8 |
| | 750 | 6 | 0.1 | 6.01 | 340.1 | 97.8 |
| | 800 | 6 | 0.3 | 18.05 | 1021.5 | 97.4 |

Notations of Table 4 were according to the following.
GWP100: 1234ze = 10 (assumption); 245fa = 950; 254pc = 30
Warming Effect Reduction Rate:
Reduction Rate (value per weight) relative to the minimum amount of CO2 gas + SF6 used, at each temperature
650° C.: $CO_2$ 2 L/min + 0.2% $SF_6$;
700° C.: $CO_2$ 4 L/min + 0.1% S
750° C.: $CO_2$ 6 L/min + 0.1% $SF_6$;
800° C.: $CO_2$ 8 L/min + 0.1% S It is clear from Table 4 that the protective gas composition (OHFC-1234ze(E), HFC-245fa or HFE-254pc, and $CO_2$) of the present invention is effective in a wide, molten metal temperature of magnesium or magnesium alloy of 650-800° C. and can greatly reduce global warming effect as compared with the case of using $SF_6$ and $CO_2$ as the protective gas composition.

Example 4

Nitrogen ($N_2$) and OHFC-1234ze(E) were used as the protective gas composition, and the experiments were conducted as in Example 1. The results are shown in Table 5.

TABLE 5

Ignition proof Effect of OHFC-1234ze(E)
OHFC-1234ze(E) (GWP100 = 10)

| Molten Metal Temp. (° C.) | Flow Rate | | Protective Gas Conc. (%) | Time [s] | | | | | | |
|---|---|---|---|---|---|---|---|---|---|---|
| | $N_2$ (L/min) | Protective Gas (mL/min) | | 0 | 30 | 60 | 90 | 120 | 150 | 180 |
| 650 | 6 | 30.25 | 0.50 | ○ | ○ | ○ | ○ | ○ | ○ | ○ |
| | 6 | 18.15 | 0.30 | ○ | ○ | ○ | ○ | ○ | ○ | ○ |
| | 6 | 12.10 | 0.20 | ○ | ○ | ○ | ○ | ○ | ○ | ○ |
| | 6 | 6.05 | 0.10 | ○ | ○ | ○ | ○ | ○ | ○ | ○ |
| | 4 | 7.89 | 0.20 | ○ | ○ | X | X | X | X | X |
| 700 | 8 | 50.23 | 0.50 | ○ | ○ | ○ | ○ | ○ | ○ | ○ |
| | 6 | 29.98 | 0.30 | ○ | ○ | ○ | ○ | ○ | ○ | ○ |
| | 6 | 19.99 | 0.20 | ○ | ○ | ○ | ○ | ○ | ○ | ○ |
| | 6 | 9.99 | 0.10 | ○ | ○ | ○ | ○ | ○ | ○ | ○ |
| | 6 | 16.04 | 0.20 | ○ | ○ | ○ | ○ | ○ | X | X |
| | 4 | 7.89 | 0.10 | ○ | ○ | ○ | X | X | X | X |

Notations of Table 5 were according to the following standards.

○: one that does not combust (pass).

Δ: one in which an ignition source is generated, but burns out immediately or does not grow (pass).

X: one in which an ignition source grows and continues to burn. X: one in which an ignition source grows and continues to burn.

One was judged as pass, in which no combustion occurs for 180 seconds, or, even if an ignition source is generated, it does not spread.

Comparative Example 1

Nitrogen ($N_2$) and $SF_6$ were used as the protective gas composition, and experiments were conducted as in Example 1.

TABLE 6

Ignition proof Effect of $SF_6$
SF6(GWP100 = 22200)

| Molten Metal Temp. (° C.) | Flow Rate $N_2$ (L/min) | Protective Gas (mL/min) | Protective Gas Conc. (%) | Time [s] 0 | 30 | 60 | 90 | 120 | 150 | 180 |
|---|---|---|---|---|---|---|---|---|---|---|
| 650 | 6 | 5.98 | 0.10 | ○ | ○ | ○ | ○ | ○ | ○ | ○ |
|  | 4 | 20.02 | 0.50 | ○ | ○ | ○ | ○ | ○ | ○ | ○ |
|  | 4 | 11.96 | 0.30 | ○ | ○ | ○ | ○ | ○ | ○ | ○ |
|  | 4 | 8.06 | 0.20 | ○ | ○ | ○ | ○ | ○ | ○ | ○ |
|  | 4 | 3.90 | 0.10 | ○ | ○ | ○ | ○ | ○ | ○ | X |
|  | 2 | 3.90 | 0.19 | ○ | ○ | ○ | ○ | ○ | ○ | X |
| 700 | 10 | 50.18 | 0.50 | X | X | X | X | X | X | X |

Notations of Table 6 were according to the following standards.
○: one that does not combust (pass).
Δ: one in which an ignition source is generated, but burns out immediately or does not grow (pass).
X: one in which an ignition source grows and continues to burn.
One was judged as pass, in which no combustion occurs for 180 seconds, or, even if an ignition source is generated, it does not spread.

At 700° C. of the present comparative example, even in case that flow rate of the carrier gas and the protective gas concentration have been increased, $N_2+SF_6$ protective gas composition is without or extremely low in ignition proof effect.

The results of Example 4 and Comparative Example 1 are put together in Table 7.

TABLE 7

Protective Gas Minimum Flow Rate for Producing Ignition proof Effect and Warming Effect Reduction Rate
A = 0.01767 m²

| Protective Gas | Molten Metal Temp. (° C.) | $N_2$ Flow Rate (L/min) | Protective Gas Conc. (%) | Protective Gas Flow Rate (mL/min) | Protective Gas Flow Rate per Molten Metal Unit Area (mL/min/m²) | Warming Effect Reduction Rate (%) |
|---|---|---|---|---|---|---|
| OHFC-1234ze | 650 | 6 | 0.1 | 6.05 | 342.4 | 99.95 |
|  | 700 | 10 | 0.1 | 9.99 | 565.4 | 99.91 |
| $SF_6$ | 650 | 6 | 0.1 | 5.98 | 338.4 | — |

GWP100: 1234ze = 10 (assumption)

Warming Effect Reduction Rate:

Reduction Rate (value per weight) relative to the minimum amount of CO2 gas + SF6 used, at each temperature 650° C.: $CO_2$ 2 L/min + 0.2% $SF_6$;

700° C.: $CO_2$ 4 L/min + 0.1% $SF_6$

It is clear from Table 7 that the protective gas composition (OHFC-1234ze(E)+$N_2$) of the present invention can greatly reduce global warming effect, as compared with the case of using $SF_6$+$CO_2$ as a protective gas composition, and has a greater effect than that of OHFC-1234ze(E)+$CO_2$ (Table 4).

The invention claimed is:

1. A method for preventing combustion of a molten magnesium/magnesium alloy in a magnesium or magnesium alloy production, comprising allowing a gas composition comprising:
   a protective gas that is a compound selected from the group consisting of 1,1,1,3,3-pentafluoropropane (HFC-245fa), 1,3,3,3-tetrafluoropropene (OHFC-1234ze), methyl 1,1,2,2-tetrafluoroethyl ether (HFE-254 pc), and mixtures thereof; and
   a carrier gas,
to flow onto a surface of the molten magnesium/magnesium alloy molten at 600-850° C.,
   wherein the gas composition is allowed to flow at a flow velocity that is sufficient for producing ignition proof effect, in a range of 5-5000 mL/min/$m^2$ in protective gas flow rate per molten metal unit area.

2. A method according to claim 1, wherein the carrier gas is selected from the group consisting of dry air, carbon dioxide, argon, helium, neon, krypton, xenon, nitrogen, and mixtures thereof.

3. A method for preventing combustion of a molten magnesium/magnesium alloy in a magnesium or magnesium alloy production, comprising allowing a gas composition comprising:
   a protective gas that is a compound selected from the group consisting of 1,1,1,3,3-pentafluoropropane (HFC-245fa), 1,3,3,3-tetrafluoropropene (OHFC-1234ze), methyl 1,1,2,2-tetrafluoroethyl ether (HFE-254 pc), and mixtures thereof; and
   a carrier gas,
to flow onto a surface of the molten magnesium/magnesium alloy molten at 600-850° C.
   wherein the gas composition is allowed to flow at a flow velocity that is sufficient for producing ignition proof effect for 180 seconds or longer when molten metal is open, in a range of 0.005-5 volume % in protective gas concentration in the carrier gas and/or 5-5000 mL/min/$m^2$ in protective gas flow rate per molten metal unit area.

4. A method according to claim 3, wherein the carrier gas is selected from the group consisting of dry air, carbon dioxide, argon, helium, neon, krypton, xenon, nitrogen, and mixtures thereof.

* * * * *